United States Patent [19]

Okamoto et al.

[11] Patent Number: 4,545,993

[45] Date of Patent: Oct. 8, 1985

[54] 1,2-BENZOPYRAN-6-YL ACETIC ACID COMPOUNDS AND PHARMACEUTICAL COMPOSITIONS CONTAINING SAID COMPOUNDS

[75] Inventors: Kaoru Okamoto; Masaki Hamada; Teikichi Kurosaki, all of Osaka, Japan

[73] Assignee: Nippon Zoki Pharmaceutical Co. Ltd., Hiranomachi, Japan

[21] Appl. No.: 400,029

[22] Filed: Jul. 20, 1982

[30] Foreign Application Priority Data

Aug. 12, 1981 [JP] Japan .................. 56-126912

[51] Int. Cl.[4] .................. A61K 31/35; C07D 311/70
[52] U.S. Cl. .................. 514/456; 549/398;
549/404; 549/405; 549/408; 549/60; 549/79;
560/55; 562/452
[58] Field of Search .................. 549/398; 424/283

[56] References Cited

PUBLICATIONS

Stabilimenti, Chem. Abstr., 88, 6721z (1978).
Maillard et al., Eur. J. Med. Chem.-Chem. Ther., 12, 161 (1977).
Birch et al., Chem. Abstr., 68, 21785d (1968).

Primary Examiner—Nicky Chan
Attorney, Agent, or Firm—Pennie & Edmonds

[57] ABSTRACT

Heterocyclic compounds comprising the formula (I):

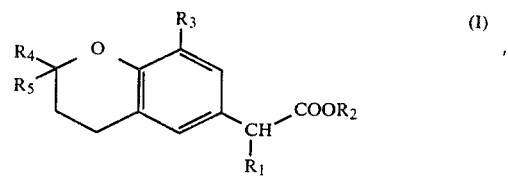

wherein:

$R_1$, $R_2$, $R_4$ and $R_5$ each are hydrogen or a lower alkyl group;

$R_3$ is hydrogen, a halogen, an alkyl group, a haloalkyl group, an alkoxy group, an alkenyl group, an alkenyloxy group, an aryl group, an aryloxy group, an acyl group or a nitro group;

and the broken line connotes a single or double bond at the $C_3$–$C_4$ position, provided that when the broken line connotes a single bond, $R_3$ is other than hydrogen; and pharmaceutically acceptable salts thereof, exhibiting antiinflammatory, antipyretic and analgesic action.

13 Claims, 2 Drawing Figures

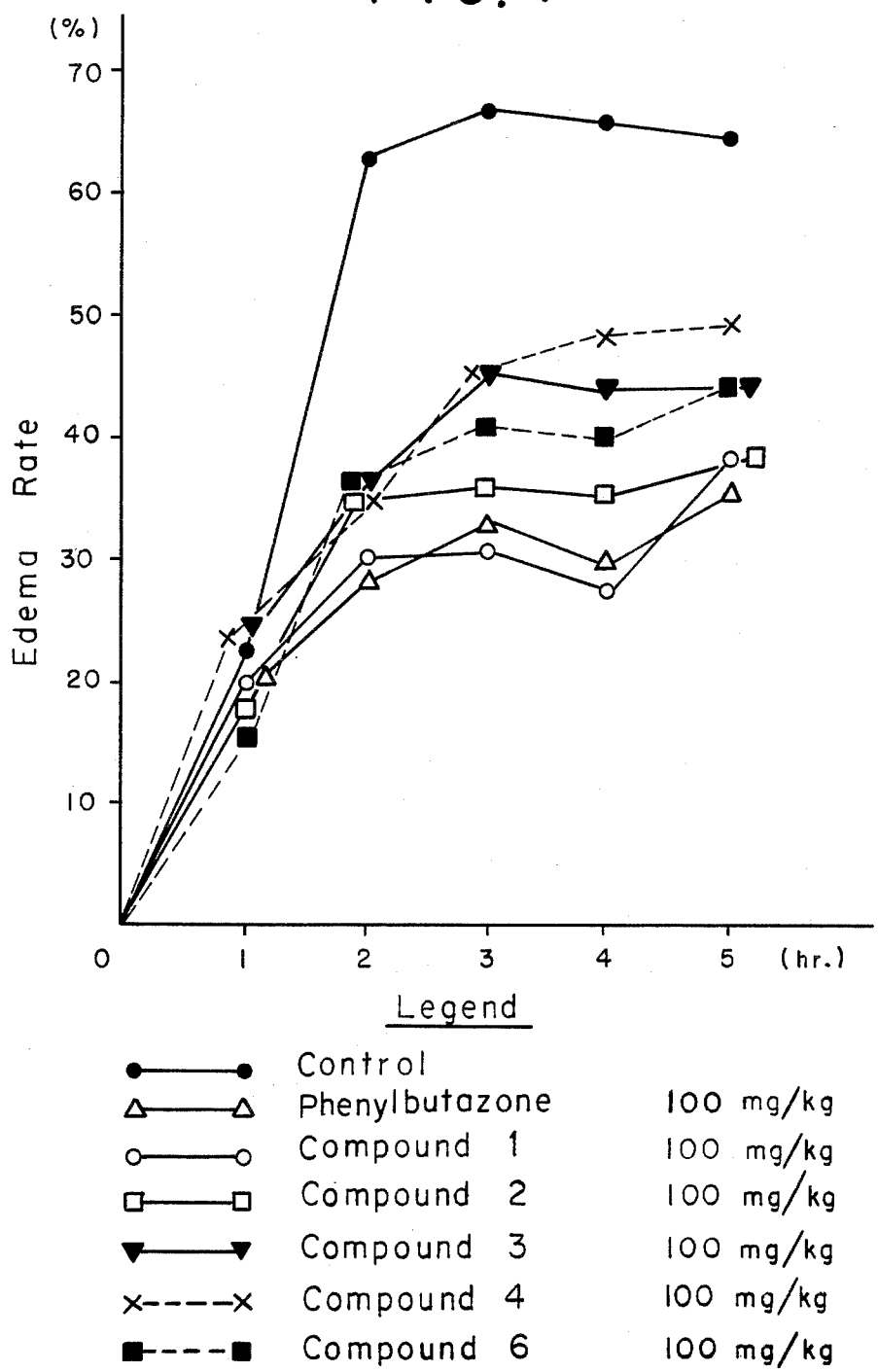

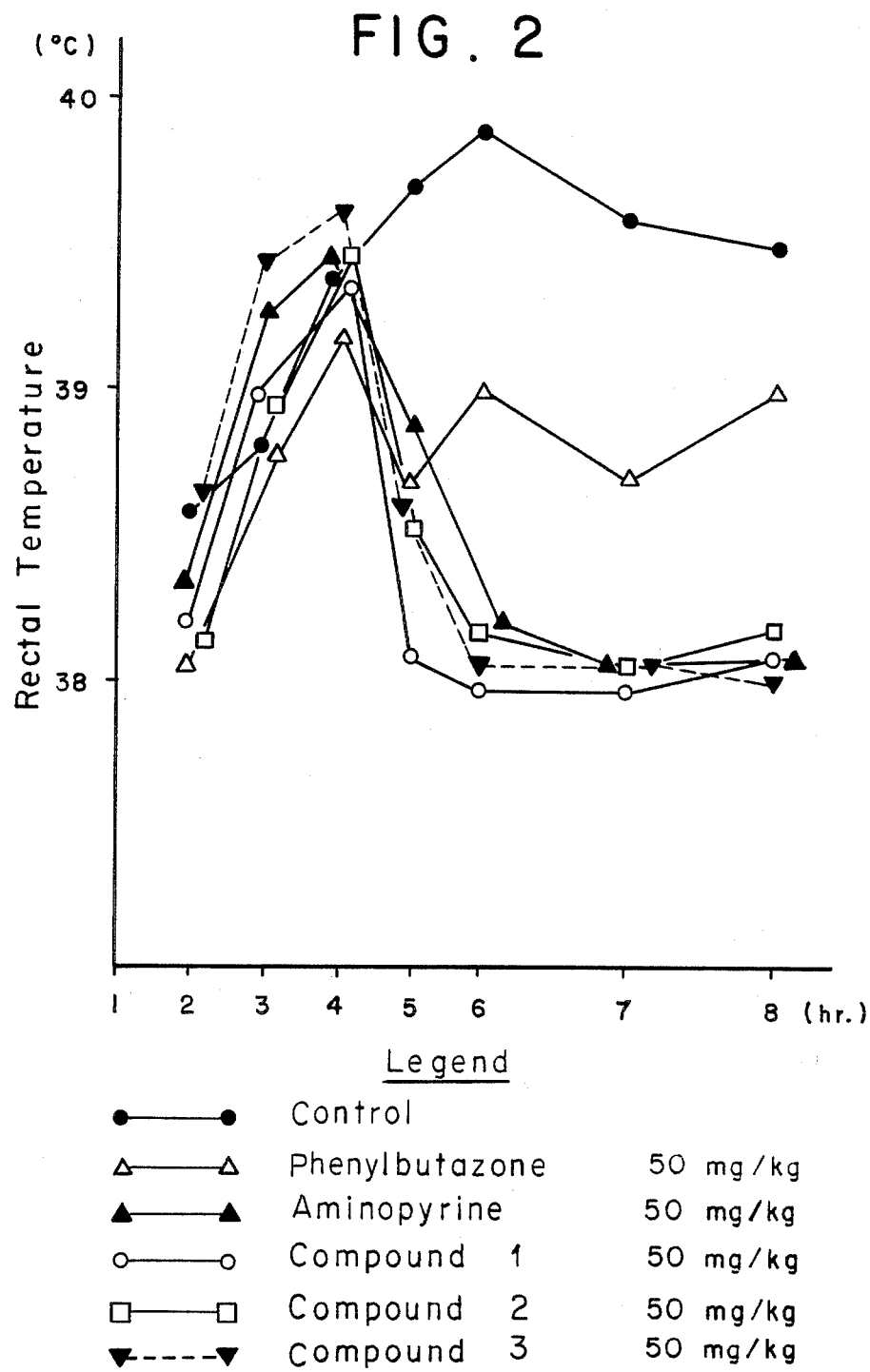

1,2-BENZOPYRAN-6-YL ACETIC ACID COMPOUNDS AND PHARMACEUTICAL COMPOSITIONS CONTAINING SAID COMPOUNDS

BACKGROUND OF THE INVENTION

The present invention relates to new heterocyclic compounds and a process for producing them, as well as to pharmaceutical compositions containing such compounds.

Compounds such as salicylates, anthranilic acid derivatives, phenylacetic acid derivates, indolylacetic acid derivatives and pyrazolones are well known as drugs exhibiting antipyretic, analgesic and antiinflammatory actions. However, the commercial success of these drugs has been hindered due to side effects experienced by the user. Known side effects created include gastrointestinal, hepatorenal and hematological disorders.

Alleviation of these adverse effects has been attempted by improving dosage forms and by modifying the chemical structure of the drugs, or more recently by other methods, e.g., the use of pro-drugs.

The present invention results from the investigation for new pharmaceutically useful compounds, comparable or superior in effectiveness to conventional non-steroid drugs, that do not create the above-mentioned side effects. As a result, new types of heterocyclic compounds were discovered and certain of these compounds, exhibiting low toxicity, have been found to be pharmaceutically useful as antiinflammatory and antipyretic-analgesic agents.

DETAILED DESCRIPTION OF THE INVENTION

The heterocyclic compounds of this invention are represented by the following general formula (I):

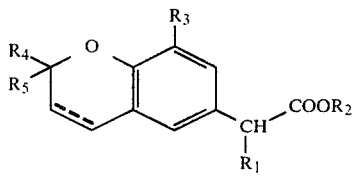

wherein $R_1$, $R_2$, $R_4$ and $R_5$ each are hydrogen or a lower alkyl group; $R_3$ is hydrogen, a halogen, an alkyl group, a haloalkyl group, an alkoxy group, an alkenyl group, an alkenyloxy group, an aryl group, an aryloxy group, an acyl group or nitro group; and the broken line connotes a single or double bond at the $C_3$–$C_4$ position, provided that when the broken line connotes a single bond, $R_3$ is other than hydrogen.

$R_1$, $R_2$, $R_4$ and $R_5$ are each further defined as hydrogen; or a straight or branched lower alkyl group, such as methyl, ethyl, propyl, iso-propyl, butyl, iso-butyl, sec-butyl, or t-butyl.

$R_3$ includes hydrogen; a halogen such as fluorine, chlorine, bromine, iodine; a straight or branched alkyl group, preferably having 1 to 8 carbon atoms, such as methyl, ethyl, propyl, iso-propyl, butyl, iso-butyl, sec-butyl, t-butyl as well as pentyl, hexyl, heptyl or octyl, including their branched isomers, each which may be optionally substituted with a cycloalkyl group such as cyclopropylmethyl, cyclobutylmethyl, cyclopentylmethyl, and cyclohexylmethyl; an alkyl group as defined by the above-mentioned group substituted with one or more halogens, haloalkyl groups such as chloromethyl, chloroethyl, fluoromethyl, fluoroethyl, bromomethyl, bromoethyl, trifluoromethyl being especially preferred; alkoxy groups corresponding to the above-mentioned alkyl groups; straight or branched alkenyl groups, preferably those with 2 to 7 carbon atoms such as vinyl, propenyl, butenyl, pentenyl, hexenyl and heptenyl, especially methallyl and allyl; alkenyloxy groups corresponding to these alkenyl groups; aryl groups such as phenyl, tolyl, xyly, biphenylyl and naphthyl; aryloxy groups corresponding to these aryl groups; acyl groups including aliphatic acyl groups such as acetyl, propionyl, butyryl, valeryl, aromatic acyl groups such as benzoyl, toluoyl, naphthoyl, cinnamoyl, and heterocyclic acyl groups such as furoyl, and thenoyl; and a nitro group.

When optical isomers exist in the above-mentioned compounds, the present invention includes any of the dl,l- and d-isomers.

The present invention also includes pharmaceutically acceptable salts of the compounds, including salts of such alkali metals as sodium or potassium; of the alkaline-earth metals such as calcium and magnesium; and with ammonium, which are especially preferred when the compounds are free carboxylic acids.

The following are representative of the heterocyclic compounds of this invention:
(8-Chloro-1,2-benzopyran-6-yl)acetic acid,
2-(8-Chlorochroman-6-yl)propionic acid,
2-(2,2-Dimethyl-8-chlorochroman-6-yl)propionic acid,
2-(8-Chloro-1,2-benzopyran-6-yl)propionic acid
2-(2,2-Dimethyl-8-chloro-1,2-benzopyran-6-yl)propionic acid,
2-(2,2-Dimethyl-1,2-benzopyran-6-yl)propionic acid,
2-(2,2-Dimethyl-8-fluoro-1,2-benzopyran-6-yl)propionic acid,
2-(2,2-Dimethyl-8-phenyl-1,2-benzopyran-6-yl)propionic acid,
2-(8-Phenyl-1,2-benzopyran-6-yl)propionic acid,
2-(2,2-Dimethyl-8-benzoyl-1,2-benzopyran-6-yl)propionic acid,
2-(8-Isopropyl-1,2-benzopyran-6-yl)propionic acid,
(2,2-Dimethyl-8-methoxy-1,2-benzopyran-6-yl)acetic acid,
2-(2,2-Dimethyl-8-thenoyl-1,2-benzopyran-6-yl)propionic acid,
(2,2-Dimethyl-8-nitro-1,2-benzopyran-6-yl)acetic acid,
(2,2-Dimethyl-8-phenoxy-1,2-benzopyran-6-yl)acetic acid,
as well as lower alkyl esters of these compounds.

In accordance with the present invention, the novel compounds are prepared as follows. The substituents have the same meanings as those in the above-mentioned general formula (I) unless otherwise stated.

A compound represented by the general formula (II):

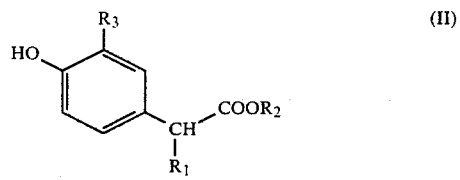

is reacted with a compound represented by the general formula (III):

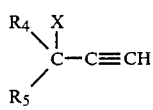

(wherein X, indicates a halogen) to give a compound represented by the general formula (IV):

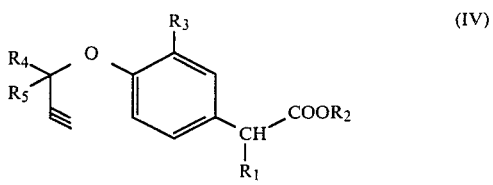

and the compound (IV) is converted by a ring closure reaction to a 1,2-benzopyran compound of this invention.

To carry out the reaction, the compounds represented by general formulae (II) and (III) are allowed to stand at room temperature or are heated at an appropriate temperature in inert solvents such as benzene, toluene, xylene, acetone, methyl ethyl ketone, diethyl ether, methyl isobutyl ketone, tetrahydrofuran, dioxane, dimethoxyethane, dimethylformamide, dimethyl sulfoxide, preferably in acetone or dimethylformamide; and in the presence of bases such as sodium carbonate, potassium carbonate, calcium carbonate, sodium bicarbonate, sodium hydroxide, potassium hydroxide, tertiary amines, preferably in the presence of potassium carbonate, to give compounds represented by the general formula (IV). Any suitable reaction promoter may be optionally added, including sodium iodide and potassium iodide.

The resulting compounds of general formula (IV) can be heated up to, for example 190°–220° C. in the presence of a suitable solvent, e.g., dimethylaniline or diethylaniline, to yield quantitative amounts of 1,2-benzopyran compounds via ring closure.

The obtained 1,2-benzopyran compounds can be reduced by any known method to produce the chroman compounds of the present invention. Typical reduction catalysts include platinum oxide, palladium charcoal or Raney Ni. Another way to obtain the chroman compounds is by reacting alkene derivatives corresponding to general formula (III), with compounds of general formula (II), and subjecting the product to acid treatment. Acids such as sulfuric acid or boron trifluoride etherate can be used in the present invention.

The resulting esters of this invention can be hydrolyzed in appropriate solvents such as water, ethanol, methanol, or mixtures thereof, in the presence of an alkali metal hydroxide, preferably sodium hydroxide or potassium hydroxide, at room temperature or under reflux for 30 minutes to 2 hours, to obtain the corresponding free carboxylic acids.

The compounds of the present invention may also be converted to their salts, if desired, by standard prior art methods.

The compounds of the present invention can be purified by usual methods such as distillation, chromatography and recrystallization. Identification is established through, inter alia, elemental analysis, melting point, IR, NMR, UV and mass spectrum, etc.

DRAWING FIGURES

Further benefits and advantages of the invention will become apparent from a consideration of the following descriptions given with reference to the accompanying drawing figures which specify and show preferred embodiments of the present invention.

BRIEF DESCRIPTION OF THE DRAWINGS

FIG. 1 illustrates antiinflammatory effects of the compounds of the present invention.

FIG. 2 illustrates antipyretic effects of the compounds of the present invention.

EXAMPLES

The following examples serve to illustrate specific embodiments of the present invention, but do not limit the scope thereof.

EXAMPLE 1

60 ml of dimethylformamide were added to 8.5 g of methyl 2-(3-fluoro-4-hydroxyphenyl)propionate, 10.7 g of potassium iodide and 11.9 g of potassium carbonate, and 6.3 ml of 3-chloro-3-methyl-1-butyne were further added dropwise, and the mixture was reacted at 75° C. for 18 hours followed by addition of water and extraction with ether. The ether solution was washed with water and a saturated solution of sodium chloride, dried over anhydrous sodium sulfate, and then the solvent was distilled off. The residue was purified by column chromatography on silica gel (benzene) to obtain 9.1 g of methyl 2-[3-fluoro-4-(1,1-dimethylpropargyloxy)-phenyl]propionate, to 9 g of which were added 45 ml of dimethylaniline and was heated under reflux at 210° C. for 3 hours. After cooling, ether was added, washed with 5% hydrochloric acid, water and saturated sodium chloride. The resulting product was treated as described above to give 7.3 g of methyl 2-(2,2-dimethyl-8-fluoro-1,2-benzopyran-6-yl)propionate.

70 ml of methanol and 7 ml of 50% potassium hydroxide were added to the obtained compound and refluxed for 1 hour; methanol was distilled off under reduced pressure; and water was added to the residue, which was washed with ether, and concentrated hydrochloric acid was added to the aqueous layer, which then was extracted with ether. The ether layer was washed with water and saturated sodium chloride, dried over anhydrous sodium sulfate and the crystals obtained were recrystallized from a mixture of n-hexane and ethyl acetate to give quantitatively 2-(2,2-dimethyl-8-fluoro-1,2-benzopyran-6-yl)propionic acid (compound 1).

The characteristic data of the compound is as follows:

mp: 96°–98° C.

IR (KBr): 3400–2100, 2970, 1700, 1635, 1619, 1582, 1488, 1379, 1272, 1211, 1142, 1055, 905, 722, 699 cm$^{-1}$

NMR (CDCl$_3$): $\delta = 1.46$ (6H, s), 1.46 (3H, d, J=7 Hz), 3.60 (1H, q, J=7 Hz), 5.62 (1H, d, J=10 Hz), 6.28 (1H, dd, J$_1$=10 Hz, J$_2$=2 Hz), 6.6–7.0 (2H, m), 11.07 (1H, br.s)

EXAMPLE 2

100 ml of dimethylformamide were added to 10.0 g of ethyl 3-methoxy-4-hydroxyphenylacetate, 11.8 g of potassium iodide and 13.1 g of potassium carbonate, and then 8.1 ml of 3-chloro-3 methyl-1-butyne were added dropwise and the mixture was stirred at 70° to 80° C. for 20 hours. After cooling, water was added to the mixture, which was extracted with ether; the ether layer was washed with water, 10% sodium hydroxide and a saturated solution of sodium chloride, and dried over anhydrous sodium sulfate; the solvent was distilled off; and the residue was purified by column chromatography on silica gel (benzene/ethyl acetate=10/1) to give 6.0 g of ethyl 3-methoxy-4-(1,1-dimethylpropargyloxy)-phenylacetate. The obtained compound was dissolved in 60 ml of dimethylaniline and refluxed at 210° to 220° C. for 4 hours, and then ether was added to the reaction mixture and, in the same manner as example 1, 5.7 g of ethyl (2,2-dimethyl-8-methoxy-1,2-benzopyran-6-yl)acetate were obtained.

6 ml of 50% potassium hydroxide were added to a solution of 5.7 g of the above compound in 60 ml of ethanol and the mixture was stirred at 70° C. for 30 minutes, then, after ethanol was distilled off, water was added to the resultant residue, which was washed with ether; and the aqueous layer was made acidic by hydrochloric acid and the crystals which separated out were recrystallized from a mixture of n-hexane and ethyl acetate to give quantitatively (2,2-dimethyl-8-methoxy-1,2-benzopyran-6-yl)acetic acid.

The characteristic data of the compound is as follows:
mp: 109°–111° C.
IR (KBr): 3500–2200, 2955, 1690, 1630, 1581, 1485, 1376, 1209, 1148, 1090, 950, 720, 640 cm$^{-1}$
NMR (Acetone-D$_6$): $\delta$=1.39 (6H, s), 3.49 (2H, s), 3.78 (3H, s) 5.66 (1H, d, J=10 Hz), 6.31 (1H, d, J=10 Hz), 6.59 (1H, d, J=2 Hz), 6.79 (1H, d, J=2 Hz), 7.8–9.5 (1H, br.)

The following compounds were obtained in accordance with Example 2:
Methyl 2-(2,2-dimethyl-8-benzoyl-1,2-benzopyran-6-yl)propionate,
Methyl 2-(2,2-dimethyl-8-phenyl-1,2-benzopyran-6-yl)propionate,
Methyl 2-(2,2-dimethyl-1,2-benzopyran-6-yl)propionate,
Methyl 2-(2,2-dimethyl-8-chloro-1,2-benzopyran-6-yl)propionate,
Methyl 2-(2,2-dimethyl-8-thenoyl-1,2-benzopyran-6-yl)propionate,
Methyl 2-(8-phenyl-1,2-benzopyran-6-yl)propionate,
Methyl 2-(8-isopropyl-1,2-benzopyran-6-yl)propionate,
Methyl 2-(8-chloro-1,2-benzopyran-6-yl)propionate,
Methyl(2,2-dimethyl-8-nitro-1,2-benzopyran-6-yl)acetate,
Methyl(2,2-dimethyl-8-phenoxy-1,2-benzopyran-6-yl)acetate,
Methyl(8-chloro-1,2-benzopyran-6-yl)acetate,
and converted to their corresponding carboxylic acids.
The products had the following characteristics:
2-(2,2-Dimethyl-8-benzoyl-1,2-benzopyran-6-yl)propionic acid;
mp: 161°–163° C.
IR (KBr): 3400–2000, 2960, 1700, 1650, 1584, 1576, 1450, 1205, 907, 738, 715, 675 cm$^{-1}$
NMR (CDCl$_3$) $\delta$=1.19 (6H, s), 1.49 (3H, d, J=7 Hz), 3.65 (1H, q, J=7 Hz), 5.53 (1H, d, J=10 Hz), 6.39 (1H, d, J=10 Hz), 7.02 (1H, d, J=2 Hz), 7.15 (1H, d, J=2 Hz), 7.2–8.0 (5H, m), 10.77 (1H, br.S)
2-(2,2-Dimethyl-8-phenyl-1,2-benzopyran-6-yl)propionic acid;
mp: 129°–131° C.
IR (KBr): 3400–2000, 2970, 1698, 1596, 1499, 1460, 1258, 1132, 940, 759, 695 cm$^{-1}$
NMR (CDCl$_3$): $\delta$=1.39 (6H, s), 1.50 (3H, d,J=7 Hz), 3.65(1H, q, J=7 Hz), 5.59 (1H, d, J=10 Hz), 6.41 (1H, d, J=10 Hz), 6.90 (1H, d, J=2 Hz), 7.10 (1H, d, J=2 Hz), 7.15–7.7 (5H, m), 9.57 (1H, br.s)
2-(2,2-Dimethyl-1,2-benzopyran-6-yl)propionic acid (compound 2);
mp: 82°–84° C.
IR (KBr): 3600–2100, 2970, 1695, 1632, 1600, 1468, 1260, 1200, 1145, 955, 765, 715 cm$^{-1}$
NMR (CDCl$_3$): $\delta$=1.38 (6H, s), 1.45 (3H, d, J=7 Hz), 3.60 (1H, q, J=7 Hz), 5.51 (1H, d, J=10 Hz), 6.24 (1H, d, J=10 Hz), 6.6–7.2, (3H, m), 11.53 (1H, s)
2-(2,2-Dimethyl-8-chloro-1,2-benzopyran-6-yl)propionic acid (compound 3);
mp: 88°–90° C.
IR (KBr): 3600–2200, 2970, 1705, 1630, 1562, 1465, 1270, 1205, 1140, 940, 900, 765, 720 cm$^{-1}$
NMR (CDCl$_3$): $\delta$=1.46 (6H, s), 1.47 (3H, d, J=7 Hz), 3.59(1H, q, J=7 Hz), 5.61 (1H, d, J=10 Hz), 6.26 (1H, d, J=10 Hz), 6.80 (1H, d, J=2 Hz), 7.11 (1H, d, J=2 Hz), 11.15 (1H, br.s)
2-(2,2-Dimethyl-8-thenoyl-1,2-benzopyran-6-yl)propionic acid;
mp: 133°–135° C.
IR (KBr): 3400–2200, 2970, 1700, 1633, 1580, 1519, 450, 1411, 1268, 1208, 1145, 903, 760, 721, 678 cm$^{-1}$
NMR (Acetone-D$_6$): $\delta$=1.30 (6H, s), 1.46 (3H, d, J=7 Hz), 3.75 (1H, q, J=7 Hz), 5.73 (1H, d, J=10 Hz), 6.45 (1H, d, J=10 Hz), 7.0–7.3 (3H, m), 7.49(1H, dd, J$_1$=4 Hz, J$_2$=1.5 Hz), 7.78 (1H, dd, J$_1$=5 Hz), J$_2$=1.5 Hz), 9.07 (1H, br.s)
2-(8-Phenyl-1,2-benzopyran-6-yl)propionic acid;
mp: 143°–145° C.
IR (KBr): 3400–2000, 1709, 1600, 1500, 1472, 1215, 1130, 1032, 895, 764, 701 cm$^{-1}$
NMR (CDCl$_3$): $\delta$=1.49 (3H, d, J-7 Hz), 3.67 (1H,q,J=7 Hz), 4.75 (2H, dd, J$_1$=3 Hz, J$_2$=1.5 Hz), 5.77 (1H, dt, J$_1$=10 Hz, J$_2$=3 Hz), 6.43 (1H, dt, J$_1$=10 Hz, J$_2$=1.5 Hz), 6.90 (1H, d, J=2 Hz), 7.10 (1H, d, J=2 Hz), 7.15–7.7 (5H, m), 9.47(1H, br.s)
2-(8-Isopropyl-1,2-benzopyran-6-yl)propionic acid;
mp: 78°–80° C.
IR (KBr): 3500–2000, 2950, 1700, 1582, 1467, 1204, 1142, 920, 705 cm$^{-1}$
NMR (CDCl$_3$): $\delta$=1.19 (6H, d, J=7 Hz), 1.47 (3H, d, J=7 Hz), 3.20 (1H, sep, J=7 Hz), 3.61 (1H, q, J=7 Hz), 4.74 (2H, dd, J$_1$=3.5 Hz, J$_2$=1.5 Hz), 5.73 (1H, dt, J$_1$=10 Hz, J$_2$=3.5 Hz), 6.37 (1H, dt, J$_1$=10 Hz, J$_2$=1.5 Hz), 6.74 (1H, d, J=2 Hz), 6.94 (1H, d, J=2 Hz), 10.97 (1H, br.s)
2-(8-Chloro-1,2-benzopyran-6-yl)propionic acid (compound 4):
mp: 97°–99° C.
IR (KBr): 3500–2100, 1700, 1635, 1560, 1472, 1324, 1220, 1138, 1029, 920, 885, 720, 685 cm$^{-1}$
NMR (CDCl$_3$): $\delta$=1.44 (3H, d, J=7 Hz), 3.58 (1H, q, J=7 Hz), 4.88 (2H, dd, J$_1$=4 Hz, J$_2$=2 Hz), 5.74 (1H, dt, J$_1$=10 Hz, J$_2$=4 Hz), 6.34 (1H, dt, J$_1$=10 Hz, J$_2$=2 Hz), 6.77 (1H, d, J=2 Hz), 7.09 (1H,d, J=2 Hz), 11.43 (1H, br.s)
(2,2-Dimethyl-8-nitro-1,2-benzopyran-6-yl)acetic acid;
mp: 149°–151° C.
IR (KRr): 3600–2200, 1705, 1635, 1610, 1568, 1520, 1265, 1230, 1140, 948, 750, 721 cm$^{-1}$
NMR (Acetone-D$_6$): $\delta$=1.48 (6H, s), 3.63 (2H, s), 5.88 (1H, d, J=10 Hz), 6.48 (1H, d, J=10 Hz), 7.24 (1H, d, J=2 Hz), 7.60 (1H, d, J=2 Hz), 9.5–10.5 (1H, br)

(2,2-Dimethyl-8-phenoxy-1,2-benzopyran-6-yl)acetic acid;

mp: 148°–150° C.

IR (KBr): 3500–2100, 1700, 1621, 1584, 1560, 1490, 1360, 1202, 1151, 835, 758, 692 cm$^{-1}$

NMR (Acetone-D$_6$): δ=1.26 (6H, s), 3.75 (2H, s), 5.84 (1H, d, J=10 Hz), 6.69 (1H, d, J=10 Hz), 6.8–7.5 (7H,m), 10.0–11.0 (1H, br)

(8-Chloro-1,2-benzopyran-6-yl)acetic acid compound 5);

mp: 137°–139° C.

IR (KBr): 3400–2000, 1690, 1637, 1599, 1562, 1478, 1301, 1225, 1217, 1136, 911, 860, 721, 689, 631 cm$^{-1}$

NMR (Acetone-D$_6$): δ=3.52 (2H, s), 4.87 (2H, dd, J$_1$=4 Hz, J$_2$=1.5 Hz), 5.83 (1H, dt, J$_1$=10 Hz, J$_2$=4 Hz), 6.40 (1H, dt, J$_1$=10 Hz, J$_2$=1.5 Hz), 6.84 (1H, d, J=2 Hz), 7.10 (1H, d, J=2 Hz), 8.34 (1H, br.s)

Example 3

10 ml of methanol and 10 mg of platinum oxide were added to 1 g of methyl 2-(2,2-dimethyl-8-chloro-1,2-benzopyran-6-yl)propionate and vigorously stirred in a stream of hydrogen for 15 minutes and then filtered, and the filtrate was distilled off to give methyl 2-(2,2-dimethyl-8-chlorochroman-6-yl)propionate. 10 ml of methanol and 1 ml of 50% potassium hydroxide were added to the compound and refluxed for 1 hour; methanol was distilled off under reduced pressure; and the crystals, obtained after adding water and acidifying by hydrochloric acid, were recrystallized from a mixture of n-hexane and ether to give quantitatively white crystals of 2-(2,2-dimethyl-8-chlorochroman-6-yl)propionic acid (compound 6).

The product had the following characteristics:

mp: 116°–118° C.

IR (KBr): 3500–2100, 2970, 1702, 1600, 1568, 1475, 1231, 1146, 1115, 920, 767, 718, 668 cm$^{-1}$

NMR (CDCl$_3$): δ=1.34 (6H,s), 1.44 (3H, d, J=7 Hz), 1.77 (2H, t, J=7 Hz), 2.74 (2H, t, J=7 Hz), 3.58 (1H, q, J=7 Hz), 6.87 (1H, d, J=Hz), 7.11 (1H, d, J=2 Hz),11.15 (1H, br.s)

The following compounds were obtained in the same way:

Methyl 2-(8-chlorochroman-6-yl)propionate, 2-(8-Chlorochroman-6-yl)propionic acid (compound 7);

mp: 135°–137° C.

IR (KBr): 3500–2000, 1700, 1565, 1480, 1422, 1322, 1230, 1130, 1058, 940, 865, 720 cm$^{-1}$

NMR (CDCl$_3$): δ=1.45 (3H, d, J=Hz), 1.98 (2H,tt, J$_1$=6 Hz, J$_2$=5 Hz), 2.77 (2H, t, J=6 Hz), 3.58 (1H, q, J=7 Hz), 4.24 (2H, t, J=5 Hz), 6.83 (1H, d, J=2 Hz), 7.09 (1H, d, J=2 Hz), 10.98 (1H, br.s)

The compounds of the present invention have new structures different from conventional non-steroid compounds and exhibit remarkably potent antiinflammatory, analgesic and antipyretic actions as well as low toxicity.

The following descriptions serve to illustrate the results obtained from animal studies.

(1) Acute toxicity

Groups of 10 male dd mice weighing some 18 g, were orally administered 800 mg/Kg of each of the examined drugs and the number of deaths up to 72 hours later was recorded.

Results are tabulated in Table 1.

TABLE 1

| Drugs | Mortality (%) |
|---|---|
| Aminopyrine | 80 |
| Phenylbutazone | 60 |
| Compound 1 | 0 |
| Compound 2 | 0 |
| Compound 3 | 0 |
| Compound 4 | 30 |
| Compound 6 | 30 |
| Compound 7 | 0 |

(2) Inhibition of plantar edema induced by carrageenin

Sixty minutes after the drug had been orally administered to groups of 5 Wistar rats, 0.1 ml of 1% carrageenin solution was subcutaneously injected into the sole. The volume of the hind foot was determined thereafter over 5 hours at intervals of 1 hour. The rate of increase in volume compared with the volume before carrageenin treatment was regarded as edema rate.

Results are shown in FIG. 1. The control indicated in the figure is 0.5% aqueous solution of carboxymethylcellulose (C.M.C.).

Furthermore, removal of sections of the stomach and intestinal tracts of the rats after the above-mentioned observation was made revealed mucosal disorder or formation of ulcer in the phenylbutazone-administered group, while no abnormality was found in any animals in the group which received the compounds of the present invention.

(3) Analgesic effects by a modified Haffner method

Groups of 10 dd mice were orally administered the examined drugs and 30 minutes later 2 mg/Kg of morphine hydrochloride, the threshhold dose, was subcutaneously injected. At 15, 30, 45 and 60 minute intervals thereafter, the root of the mouse's tail was squeezed with a Kocher's forceps. The number of animals that did not exhibit pseudopain reactions was recorded and among the four independent determinations, the determination with the largest number of responding animals was used for evaluation.

Results are tabulated in Table 2.

TABLE 2

| Drugs | Analgesic effects (%) | |
|---|---|---|
|  | 50 mg/Kg | 100 mg/Kg |
| Aminopyrine | 20 | 55 |
| Compound 1 | 40 | 70 |
| Compound 2 | 25 | 50 |
| Compound 3 | 20 | 65 |
| Compound 4 | 30 | 55 |
| Compound 5 | 35 | 70 |
| Compound 6 | 30 | 60 |

(4) Analgesic effects by acetic acid writhing test

Thirty minutes after the examined drug was orally given, 0.1 ml/10 g of 0.6% acetic acid was intraperitoneally administered to groups of 10 male dd mice weighing some 18 g. The number of stretching was calculated during an observation period of 15 to 20 minutes after acetic acid treatment. The average inhibition rate of stretching among 8 animals was regarded as the inhibition rate of the drug, excluding 2 animals showing maximum and minimum numbers of stretching.

Results are tabulated in Table 3.

TABLE 3

| Drugs | Analgesic effects (%) | |
|---|---|---|
| | 50 mg/Kg | 100 mg/Kg |
| Aminopyrine | 18 | 57 |
| Compound 1 | 59 | 76 |
| Compound 2 | 44 | 76 |
| Compound 4 | 36 | 61 |
| Compound 6 | 27 | 68 |

(5) Antipyretic effects

After the normal rectal temperature was measured, 400 mg/Kg of beer yeast was subcutaneously injected to female Wistar rats weighing 165–185 g. The body temperature of the animals was measured at one hour intervals after the yeast treatment. The animals which exhibited appreciable rise in the body temperature were selected to make groups of 10 animals. The examined drug was orally administered to the selected animals 4 hours after the yeast treatment and, during the 4 hours thereafter, measurements of the temperature were made at one hour intervals to examine antipyretic effect.

As shown in FIG. 2, the compounds of the present invention exhibited excellent antipyretic activity. The control indicated in the figure is 0.5% aqueous solution of carboxymethylcellulose (C.M.C.).

The above-mentioned animal experiments clearly indicate that the compounds of the present invention have excellent antiinflammatory, analgesic and antipyretic actions. Therefore, these compounds are therapeutically valuable as antiinflammatory, analgesic and antipyretic agents against various inflammations such as those caused by rheumatic diseases, arthritis, and other inflammations accompanied by a variety of redness, fever, swelling and pain, against painful diseases and manifestations such as acute and chronic pains, neuralgia, pains accompanied by inflammation, trauma and lumbago, and against a variety of symptoms accompanied by fever.

The compounds of the present invention can be made into pharmaceuticals by combination with appropriate medicinal carriers or diluents, and dosage forms of solids, semisolids, liquids or gases can be prepared in a usual way for oral or non-oral administration.

In preparing pharmaceutical dosage forms, the compounds of the present invention may be used in the form of their pharmaceutically acceptable salts, and they also can be used alone or in appropriated association thereof, as well as in combination with other pharmaceutically active components.

When the compounds are applied orally, they may be used alone or combined with appropriate fillers to make tablets or capsules, e.g., with conventional bases such as lactose, mannitol, corn starch, potato starch, with binders such as crystalline cellulose, cellulose derivatives, acacia, corn starch or gelatin, with disintegrators such as corn starch, potato starch or sodium carboxymethylcellulose, and with lubricants such as talc and magnesium stearate. They also can be combined with ointment bases such as vaseline, paraffin, plastibase, simple ointment, hydrophilic ointment, hydrophilic petrolatum, and hydrophilic plastibase to make ointments.

Further, the compounds of the present invention may be mixed thoroughly with a variety of bases such as emulsifying bases or water-soluble bases to give suppositories.

Regarding injectable forms, these compounds can be administered subcutaneously, intramuscularly or intravenously as solutions or suspensions in aqueous solvents or non-aqueous solvents such as vegetable oils, synthetic aliphatic acid glycerides, esters of higher aliphatic acids and propylene glycol.

When utilized as inhalation or aerosol preparations, the compounds of the present invention in the form of a liquid or minute powder can be placed into an aerosol container, with gas or liquid spraying agents, and with conventional adjuvants such as humidifying or dispersing agents added, if necessary. The compounds of the present invention also may be applied as pharmaceuticals for a neblizer or an atomizer.

Poultices can be prepared by mixing the compounds with mentha oil, concentrated glycerin, kaolin, or other suitable additives. Liniments can be prepared by adding fatty oils, essential oils, and other known additives, and if necessary, emulsifying agents such as stearic acid and oleic acid.

The desirable dose of the compounds of the present invention varies with the subject, method and period of administration, but generally it is recommended that the dose be orally administered to an adult in the amount of 10 to 3,000 mg of these compounds daily to obtain the desired effects. One to several units of the unit preparation containing the compounds of the present invention in appropriate amount may be administered.

As for non-oral administration (e.g. for injectional forms), doses on the order of one tenth to one third of the above oral dose are desirable as daily doses.

Some prescriptions of the pharmaceutical compositions are shown below as examples which contain as active ingredients the compounds of the present invention. These examples, however, do not limit the present invention.

| Prescription example 1. (tablet) | |
|---|---|
| Components | Content of a tablet (mg) |
| an invented compound | 50 |
| lactose | 130 |
| corn starch | 60 |
| magnesium stearate | 10 |
| Total | 250 mg |

| Prescription example 2. (capsule) | |
|---|---|
| Components | Content of a capsule (mg) |
| an invented compound | 100 |
| lactose | 200 |
| Total | 300 mg |

| Prescription example 3. (injection) | |
|---|---|
| Components | Content of an ampoule (mg) |
| an invented compound | 10 |
| sodium chloride | proper amount |
| distilled water for injection | proper amount |
| Total | 1 ml |

| Prescription example 4. (ointment) | |
|---|---|
| Components | Weight (g) |
| an invented compound | 1 |
| emulsified wax | 30 |
| white petrolatum | 50 |
| liquid paraffin | 20 |
| Total | 101 |

| Prescription example 5. (suppository) | |
|---|---|
| Components | Content of a suppository (mg) |
| an invented compound | 20 |
| cacao butter | 1980 |
| Total | 2000 mg |

| Prescription example 6. (aerosol) |
|---|

-continued

| Components | Weight (%) |
|---|---|
| an invented compound | 1 |
| isopropyl myristate | 1 |
| dichlorodifluoromethane | 39 |
| dichlorotetrafluoroethane | 59 |
| Total | 100% |

Prescription example 7. (poultice)

| Components | Content |
|---|---|
| an invented compound | 10 g |
| conc. glycerin | 450 g |
| mentha oil | 0.5 ml |
| kaolin | 540 g |
| Total | 1000 g |

Prescription example 8. (liniment)

| Components | Content |
|---|---|
| an invented compound | 10 g |
| potash soap | 80 g |
| camphor | 20 g |
| thyme oil | 4 ml |
| mentha oil | 6 ml |
| ammonia water | 50 ml |
| ethanol | 840 ml |
| purified water | proper amount |
| Total | 1000 ml |

We claim:

1. A heterocyclic compound having the formula (I):

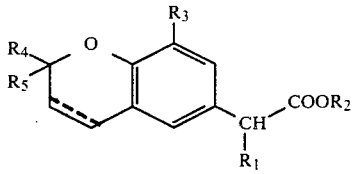

wherein:
$R_1$, $R_2$, $R_4$ and $R_5$ each are hydrogen or a lower alkyl group;
$R_3$ is a halogen; the broken line connotes a double bond at the $C_3$–$C_4$ position,
or pharmaceutically acceptable salt thereof.

2. A heterocyclic compound or pharmaceutically acceptable salt thereof according to claim 1, wherein $R_1$, $R_2$, $R_4$, and $R_5$ each are hydrogen, a methyl group, an ethyl group, a propyl group, or a butyl group.

3. A heterocyclic compound or pharmaceutically acceptable salt thereof according to claim 2, wherein:
$R_1$ is hydrogen or a methyl group;
$R_2$ is hydrogen, a methyl group, or an ethyl group; and
$R_4$ and $R_5$ each are hydrogen or a methyl group.

4. A heterocyclic compound or pharmaceutically acceptable salt thereof according to claim 3 wherein $R_2$ is hydrogen.

5. A heterocyclic compound according to claim 3 or 4 which is
2-(2,2-dimethyl-8-fluoro-1,2-benzopyran-6-yl)propionic acid,
2-(2,2-dimethyl-8-chloro-1,2-benzopyran-6-yl)propionic acid,
2-(8-chloro-1,2-benzopyran-6-yl)propionic acid, (8-chloro-1,2-benzopyran-6-yl)acetic acid, or pharmaceutically acceptable salt thereof.

6. An antiinflammatory, antipyretic or analgesic composition which comprises a pharmaceutical diluent and an effective amount of at least one compound or pharmaceutically acceptable salt thereof according to claim 1.

7. An antiinflammatory, antipyretic or analgesic composition which comprises a pharmaceutical diluent and an effective amount of at least one compound or pharmaceutically acceptable salt thereof according to claim 2.

8. An antiinflammatory, antipyretic or analgesic composition which comprises a pharmaceutical diluent and an effective amount of at least one compound or pharmaceutically acceptable salt thereof according to claim 3 or 4.

9. An antiinflammatory, antipyretic or analgesic composition which comprises a pharmaceutical diluent and an effective amount of at least one compound or pharmaceutically acceptable salt thereof according to claim 5.

10. A method for treating inflammation or pain which comprises administering an effective amount of at least one heterocyclic compound or pharmaceutically acceptable salt thereof according to claim 1 or antiinflammatory, antipyretic, or analgesic action.

11. A method for treating inflammation or pain which comprises administering an effective amount of at least one heterocyclic compound or pharmaceutically acceptable salt thereof according to claim 2 for antiinflammatory, antipyretic, or analgesic action.

12. A method for treating inflammation or pain which comprises administering an effective amount of at least one heterocyclic compound or pharmaceutically acceptable salt thereof according to claim 3 or 4 for antiinflammatory, antipyretic, or analgesic action.

13. A method for treating inflammation or pain which comprises administering an effective amount of at least one heterocyclic compound or pharmaceutically acceptable salt thereof according to claim 5 for antiinflammatory, antipyretic, or analgesic action.

* * * * *

UNITED STATES PATENT AND TRADEMARK OFFICE
CERTIFICATE OF CORRECTION

PATENT NO. : 4,545,993

DATED : October 8, 1985

INVENTOR(S) : Kaoru Okamoto et al.

It is certified that error appears in the above-identified patent and that said Letters Patent is hereby corrected as shown below:

Column 12, line 36, "claim 1 or" should be --claim 1 for--.

Signed and Sealed this

Seventh Day of January 1986

[SEAL]

Attest:

DONALD J. QUIGG

Attesting Officer     Commissioner of Patents and Trademarks